(12) United States Patent
Gondal et al.

(10) Patent No.: US 11,415,582 B2
(45) Date of Patent: Aug. 16, 2022

(54) METHOD FOR DETECTING AND TREATING COLON CANCER BY MEASURING HEAVY METAL CONCENTRATIONS

(71) Applicants: King Fahd University of Petroleum and Minerals, Dhahran (SA); Imam Abdulrahman Bin Faisal University, Dammam (SA)

(72) Inventors: Muhammad Ashraf Gondal, Dhahran (SA); Munirah A. Almessiere, Dammam (SA); Bilal A. Gondal, Champaign, IL (US)

(73) Assignees: King Fahd University of Petroleum and Minerals, Dhahran (SA); Imam Abdulrahman Bin Faisal University, Dammam (SA)

( * ) Notice: Subject to any disclaimer, the term of this patent is extended or adjusted under 35 U.S.C. 154(b) by 426 days.

(21) Appl. No.: 16/662,834

(22) Filed: Oct. 24, 2019

(65) Prior Publication Data

US 2021/0123915 A1  Apr. 29, 2021

(51) Int. Cl.
*G01N 33/574* (2006.01)
*G01N 33/483* (2006.01)
*G01N 21/31* (2006.01)
*G01N 33/20* (2019.01)

(52) U.S. Cl.
CPC ... *G01N 33/57419* (2013.01); *G01N 21/3103* (2013.01); *G01N 33/20* (2013.01); *G01N 33/4833* (2013.01)

(58) Field of Classification Search
CPC ......... G01N 33/57419; G01N 21/3103; G01N 33/20; G01N 33/4833
See application file for complete search history.

(56) References Cited

U.S. PATENT DOCUMENTS

| 5,757,484 | A | * | 5/1998 | Miles | ........... | G01N 21/718 |
| | | | | | | 356/318 |
| 7,092,087 | B2 | | 8/2006 | Kumar et al. | | |
| 2018/0143197 | A1 | | 5/2018 | Gabor Miklos | | |

FOREIGN PATENT DOCUMENTS

| CN | 10816184 A | | 6/2018 |
| CN | 108169184 | * | 6/2018 |
| WO | 2012/135227 A2 | | 10/2012 |

OTHER PUBLICATIONS

Laser induced breakdown spectroscopy for the diagnosis of several malignant tissue samples. F. Ghasemi, P. Parvin, J. Reif, S. Abachi, M. R. Mohebbifar, and M. R. Razzaghi Journal of Laser Applications 29, Apr. 2005 (2017) (Year: 2017).*

Qualitative and quantitative analysis of human nails to find correlation between nutrients and vitamin D deficiency using LIBS and ICP-AES M.A. AlmessiereR. AltuwiriqiM.A. GondalR.K. AlDakheelH. F. Alotaibi Taianta 185 (2018) 61-70 (Year: 2018).*

(Continued)

*Primary Examiner* — Brian R Gordon
*Assistant Examiner* — Dwan A Gerido
(74) *Attorney, Agent, or Firm* — Oblon, McClelland, Maier & Neustadt, L.L.P.

(57) ABSTRACT

Method for detecting colon or colorectal cancer by measuring heavy metal concentrations in colon or colorectal tissue using laser-induced breakdown spectroscopy (LIBS).

11 Claims, 11 Drawing Sheets

(56) References Cited

OTHER PUBLICATIONS

Spectroscopic detection of health hazardous contaminants in lipstick using laser induced breakdown spectroscopy M.A. Gondal, Z.S. Seddigi, M.M. Nasr, B. Gondal Journal of Hazardous Materials 175 (2010) 726-732 (Year: 2010).*
Gondal, et al. ; Laser produced plasma diagnosis of carcinogenic heavy metals in gallstones ; Journal of Analytical Atomic Spectrometry 31 ; Nov. 27, 2015 ; 10 Pages.
Gondal , et al. ; Gallbladder Stones Analysis Using Pulsed UV Laser Induced Breakdown Spectroscopy ; Journal of Medical and Bioengineering vol. 5, No. 2 ; Apr. 2016 ; 4 Pages.
El-Sherbini ; Impact of Physics on Medical Sciences and Applications: Lasers and Nanotechnology ; Journal of Medical Physics and Applied Sciences, vol. 1, No. 1:5 ; Mar. 8, 2016 ; 15 Pages.
Kumar, et al. ; Characterization of malignant tissue cells by laser-induced breakdown spectroscopy ; Applied Optics, vol. 43, No. 28 ; Oct. 2004 ; 5 Pages.

\* cited by examiner

FIG.7A 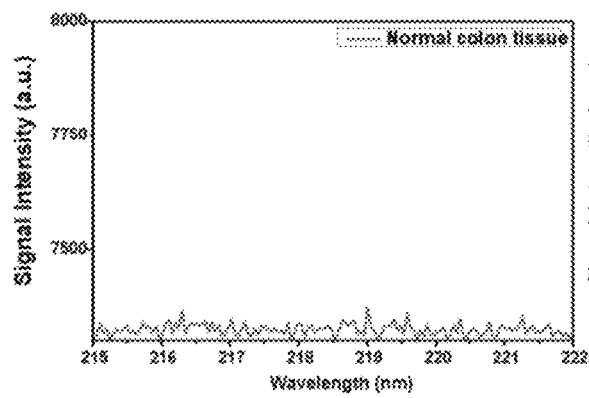 FIG.7B 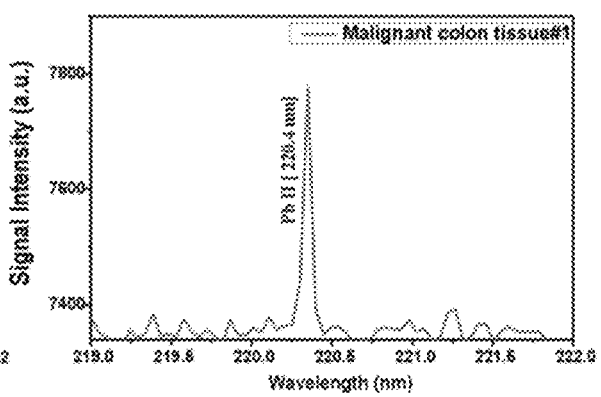
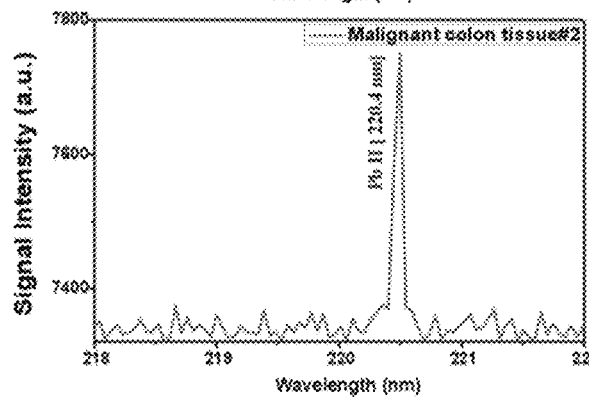 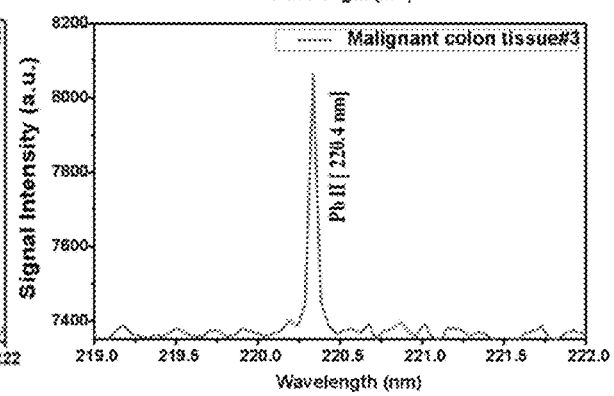
FIG.7C  FIG.7D

FIG.8A
FIG.8B
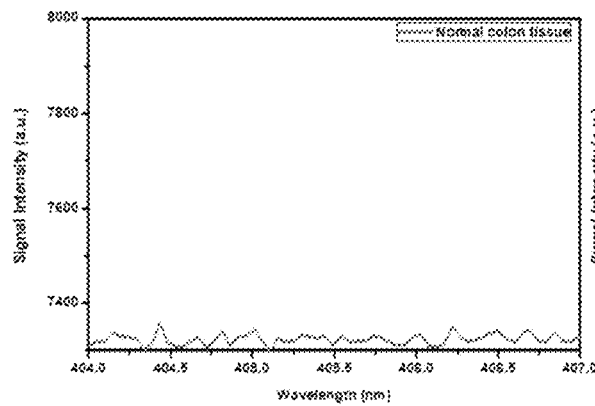
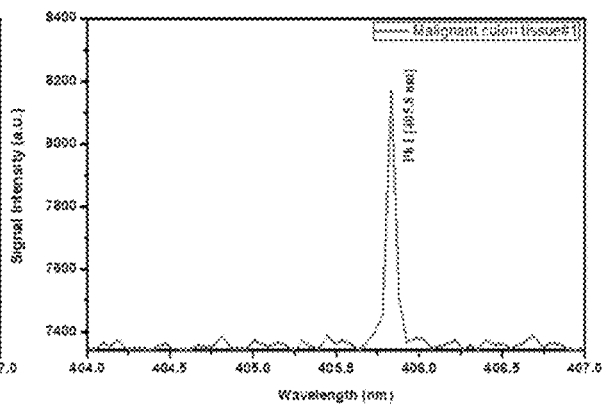
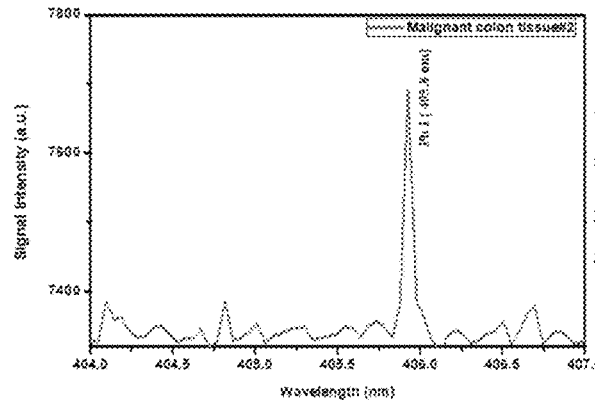
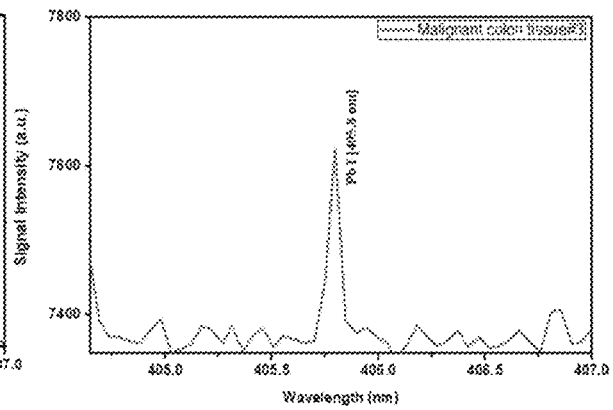
FIG.8C
FIG.8D

FIG.9A
FIG.9B
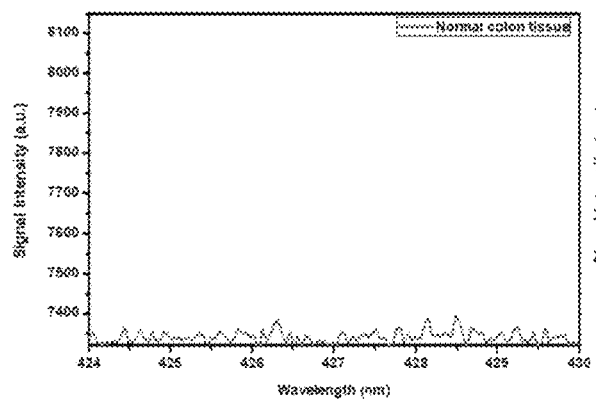
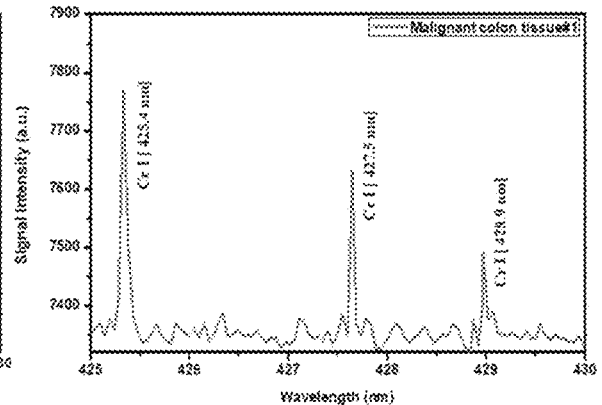
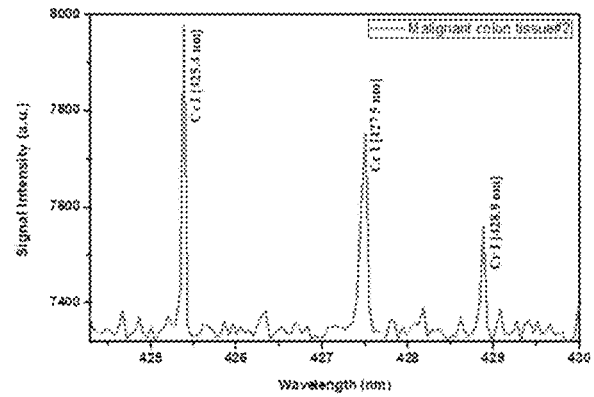
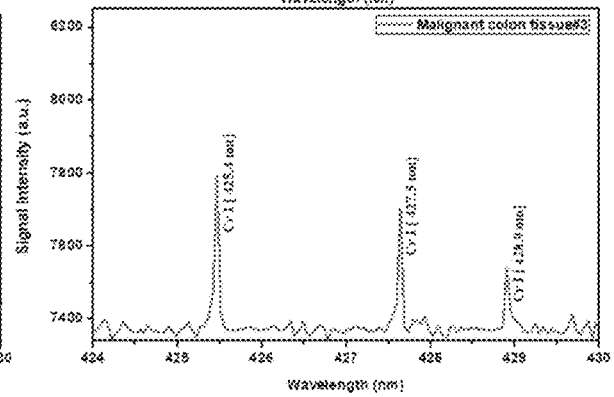
FIG.9C
FIG.9D

METHOD FOR DETECTING AND TREATING COLON CANCER BY MEASURING HEAVY METAL CONCENTRATIONS

STATEMENT OF ACKNOWLEDGEMENT

The support of King Fand University of Petroleum and Minerals (KFUPM) under project # RG 1421 is gratefully acknowledged.

BACKGROUND OF THE INVENTION

Field of the Invention

The invention pertains to the field of oncology.

Description of Related Art

Cancer remains a disease of high morbidity and mortality, affecting millions across the globe. Owing to the difficulties in diagnosing certain types of cancers in the early stage, and the limited treatments available, people continue to die every year. However, the ability to identify and diagnosis some types of cancers has improved dramatically due to increasing investment in pharmaceutical treatments and favorable results from drug trials and other advancements in medical technology. Nevertheless, many conventional diagnostic methods are insensitive or inaccurate and may even produce conflicting results. Thus, there is a need for more advanced diagnostic techniques that offer a higher probability of achieving sensitive, more reliable, robust and meaningful data.

Numerous studies applying different techniques have been carried out to classify malignant and non-malignant cells. Several such techniques depend on the differentiation between proteins or the categorization of abnormal cellular morphology. However, these techniques exhibit common drawbacks such as being time consuming, expensive, or requiring lengthy processes for sample preparation.

Laser-induced breakdown spectroscopy (LIES) has been applied to study human tissues or systems relating to human health, such as teeth, bones, blood, and other fluid samples, or the bacteria, molds, and yeasts that may affect human bodies and cause diseases; Almessiere, M. A, et al., *Qualitative and quantitative analysis of human nails to find correlation between nutrients and vitamin D deficiency using LIBS and ICP-AES*, Talanta 185(2018) 61-70, incorporated herein by reference in its entirety; Hanna Sas-Nowosielska et al., *Heavy metals in the cell nucleus—role in pathogenesis*, Acta Biochim Pol. 62 (2015) 7-13, incorporated herein by reference in its entirety. In the LIES technique, qualitative analysis of the plasma spectral lines are conducted, in which the intensities of these lines are proportional to the element concentrations in a sample, which determines whether this tissue is normal or contaminated; M. A. Gondal, et al., *Spectroscopic detection of health hazardous contaminants in lipstick using Laser induced breakdown spectroscopy*, J Hazard Mater 175 (2010) 726-732, incorporated herein by reference in its entirety. LIES has recently been applied to the study of human malignancies to detect certain specific concentrations of elements such as calcium and magnesium in malignant tissues as compared to non-neoplastic tissues; M. A. Gondal, et al., *Detection of lead in paint samples synthesized locally using-laser-induced breakdown spectroscopy*, J. Environ. Sci. Health C 46(1) (2011) 1-8, incorporated herein by reference in its entirety. A nanosecond LIES system has been applied to obtain real-time tissue information for a laser surgery process; Gondal et al. (2015) id. Chen et al. applied LIES to the diagnosis of lymphoma and multiple myeloma by ablation of the human serum deposited onto filter papers, and detected the atomic spectral lines of Ca, Na, K, H, O, and N; Xue Chen, et al., *Diagnosis of human malignancies using laser-induced breakdown spectroscopy in combination with chemometric methods*, Spectrochim Acta Part B At Spectrosc. 139 (2017) 63-69. Work has been performed using biological fluids or other modes of detecting particular elements; CN108169184A; WO2012135227A2; U.S. Pat. No. 7,092,087B2; US20180143197A1; Gondal, et al. (2015) or Gondal, et al. (2016).

There is a need for a method to diagnose colon-related illnesses based on a correlation between heavy metal accumulation in colon tissue within a sensitivity range of about 1 microgram/mL (1 ppb), preferably using LIBS. Accordingly, it is one object of the present disclosure to provide a sensitive and accurate way to diagnose or prognose colon cancer in human tissue using a calibration-free LIES technique for the quantitative analysis of cancerous and normal colon tissue samples.

SUMMARY OF THE INVENTION

In view of the above-mentioned drawbacks and limitations of previous procedures, the inventors sought to develop a highly sensitive test for colon or colorectal cancer based on more sensitive detection of heavy metals in colon or colorectal tissue. Embodiments of this method include but are not limited to the following.

One embodiment of the invention is directed to a method for distinguishing normal, non-cancerous colon or colorectal tissue from cancerous colon or colorectal tissue comprising: applying induced breakdown spectroscopy ("LIBS") to one or more test samples of colon or colorectal tissue, comparing a signal intensity for at least one heavy metal in the test sample of colon or colorectal tissue from a subject with the signal intensity for said heavy metal in a control sample, and selecting a subject having, or at risk of having, colon or colorectal cancer when the signal intensity for the heavy metal in the test sample is greater than that for the same heavy metal in the control sample; and, optionally treating the selected subject for colon cancer or colorectal cancer.

In some embodiments of the disclosed methods, the tissue samples are colon or colorectal tissue. Examples of tissue samples include polyps, not-inflamed or inflamed colon or colorectal tissue, tissue samples from a subject having a history or genetic disposition to colon cancer or colorectal cancer, such as a subject who has a parent, sibling or child having colon cancer or a subject whose genomic DNA or single-nucleotide polymorphisms indicate a higher than normal risk for colon cancer or colorectal cancer.

In some embodiments of this method the heavy metal or metal detected is cerium, chromium, lead or mercury. In other embodiments, the method as disclosed herein may be performed by measuring the intensities of other elements, such as Ca, K or Na in colon or colorectal tissue samples or such measurements may be performed in conjunction with measuring of intensities of toxic heavy metals such as Cr, Pb, or Hg or the metal Ce. One example of such a method is one that further comprises comparing signal intensity of at least one of calcium (Ca), potassium (K) or sodium (Na) in the test sample of colon or colorectal tissue with the intensity of the same elements in the control sample; and selecting a subject having, or at risk of having, colon or colorectal cancer when the signal intensity for the Ca, K or Na in the test sample is greater than that for the same element in the control sample.

In some embodiments, the method disclosed herein can measure a degree risk of developing colon or colorectal cancer based on the relative amounts of a heavy metal or mineral detected in a tissue sample. For example, as shown herein lead levels in patients with colon cancer around 2.7 µg/L, chromium levels around 14.6 µg/L, and cerium levels around 3.2 µg/L. Thus, values for these elements falling within these ranges would indicate the presence of colon or colorectal cancer or a high risk of it, while values between the control (normal tissue) values and those of patients with colon cancer would indicate a proportionately lower degree of risk, for example, 90, 80, 70, 60, 50, 40-, 30, 20, 10 or <10% of the risk of a patient having a value within the range described for patients with colon cancer.

In one embodiment, the relative risk can be calculated as: [concentration of heavy metal or element in tested sample]÷([value or average value of heavy metal concentration in colon cancer or colorectal cancer patients]÷[control value or average control value of concentration in normal tissue]). Preferably, the value for the tested subject is compared to a value or average value from cancer patients having the same risk factors, such as family history or genetic disposition, or of a similar age and sex, as the tested subject and control values are also from those from a matched normal subject. The safe permissible limits for Cr, Hg and Lead are 0.05, 0.01 and 0.1 µg/L, respectively. Hence any appreciable rise in the level of these heavy metals above these levels in colon tissue found is indicative of causing cancer or risk of colon cancer in long term exposure.

In some embodiments of the method disclosed herein, the heavy metal is cerium (Ce) and atomic lines (or peak value) at 566.9, 567.7, 569.9 and/or 571.9 nm are detected, wherein a greater intensity of Ce in a test sample compared to a control (normal colon or colorectal tissue) indicates colon or colorectal cancer or a risk thereof.

In some embodiments of the method disclosed herein, wherein the heavy metal is chromium (Cr) and atomic lines at Cr (I) 425.4, 427.5, 428.9, and/or 527.5 nm are detected, wherein a greater intensity of Cr in a test sample compared to a control (normal colon or colorectal tissue) indicates colon or colorectal cancer or a risk thereof.

In some embodiments of the method disclosed herein, wherein the heavy metal is mercury (Hg) and atomic lines at 253.7, 435.8 and/or 567.7 nm are detected, wherein a greater intensity of Hg in a test sample compared to a control (normal colon or colorectal tissue) indicates colon or colorectal cancer or a risk thereof for long term exposure of Hg.

In some embodiments of the method disclosed herein, wherein the heavy metal is lead (Pb) and atomic lines at 220.4 and/or 405.8 nm are detected, wherein a greater intensity of Pb in a test sample compared to a control (normal colon or colorectal tissue) indicates colon or colorectal cancer or a risk thereof.

In some embodiments of the methods disclosed herein, the method will exhibit a sensitivity to detect the one or more heavy metals, metals such as Ce, or other elements within a range of at least 0.5, 0.75, 1.0, 2, 3, 4, 5, 6, 7, 8, 9, to 10 µg/L in a tissue sample, preferably at a sensitivity of at least above 1 µg/L.

Some embodiments of the method disclosed herein will perform LIBS using a laser intensity ranging from about 25, 30, 35, 40, 45, or 50 mJ, preferably about 35 mJ. LIBS may be performed using at least 5, 10, 15, 20, 25, 30, 35, 40, 45, or 50 laser pulses with time delays ranging between 50, 100, 150, 200, 250, 300 or 350 ns, preferably LIBS will be performed using about 15 pulses with a time delay of about 200 ns.

In some embodiments, different conditions may be used with respect to time delay as different upper energy levels responsible for emission and life time of excited state depend on Aik (Einstein coefficient, Equation 1). LIBS signal intensity depends on the incident laser energy and detection limit is dependent on the signal to noise ratio for different number of accumulations (number of laser pulses). More accumulations averaging means less noise.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIGS. 7A-7D Atomic lines of Pb I 220.4 nm in malignant (FIGS. 7B-7D) (FIGS. 8B-8D) and normal (FIG. 7A) tissues.

FIGS. 8A-8D. Atomic line of Pb I 405.8 nm in malignant and normal (FIG. 8A) tissues.

FIGS. 9A-9D. Atomic lines of Cr I 425.4, 427.5, and 428.9 nm in malignant (FIGS. 9B-9D) and normal (FIG. 9A) tissues.

DETAILED DESCRIPTION OF THE INVENTION

Figure 1:
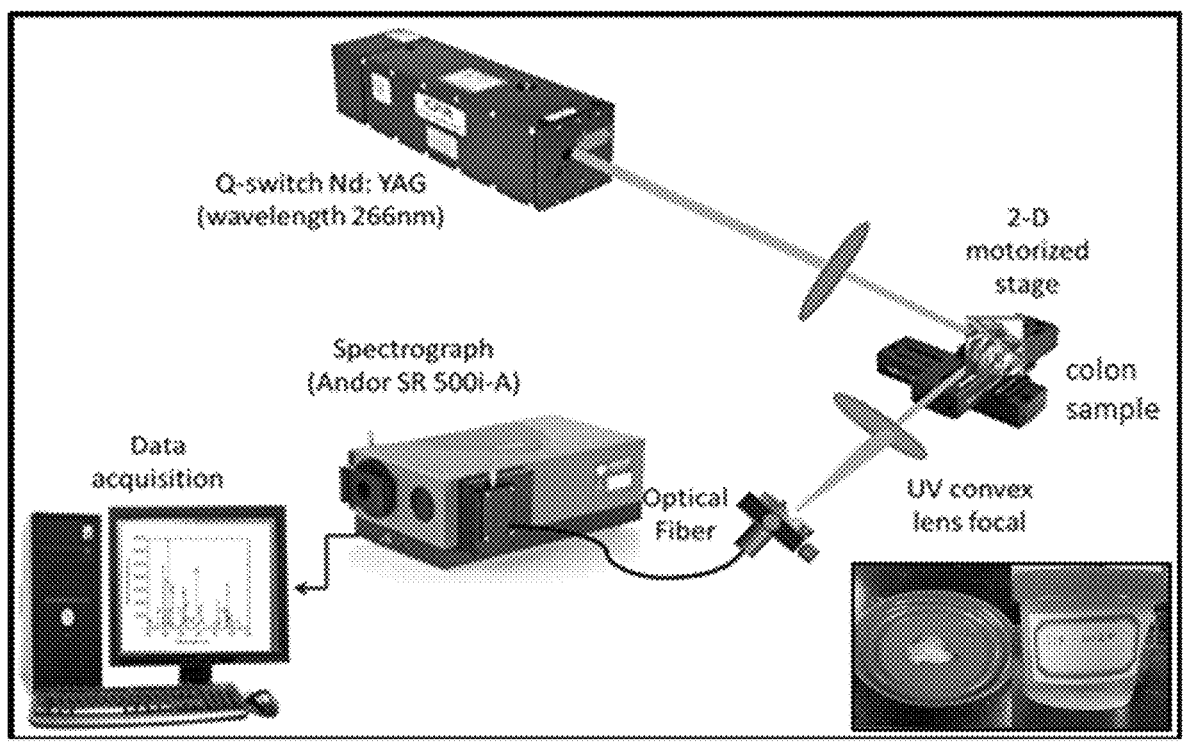
FIG. 1 Schematic of LIBS setup, where the inset shows an image of a colon sample.

Colon cancer is a type of cancer that begins in the large intestine (colon) but as defined herein includes colorectal cancer which develops in the rectum. The colon is the final part of the digestive tract. Colon cancer typically affects older adults, though it can occur at any age. It usually begins as small, noncancerous (benign) clumps of cells called polyps that form on the inside of the colon. Over time some of these polyps can become colon cancers. Polyps may be small and produce few, if any, symptoms. For this reason, doctors recommend regular screening tests to help prevent colon cancer by identifying and removing polyps before they turn into cancer.

In some embodiments, the method disclosed herein may use samples of colon tissue taken from the ascending colon, the transverse colon, the descending colon and/or the sigmoid colon. Biopsies or tissue samples from the colon may be apparently normal, non-neoplastic colon tissue or neoplastic or apparently neoplastic tissue. A sample may be obtained from inflamed or non-inflamed colon lining tissue. It may be taken from an abscess or from scar tissue in the colon. A sample may be a polyp. Non-neoplastic polyps include hyperplastic polyps, inflammatory polyps, juvenile polyps, hamartomatous polyps, Peutz-Jeghers polyps, or lymphoid polyps. Neoplastic polyps include adenomas and serrated types.

Samples. In some embodiments the method disclosed herein may be applied to tissues of the gastrointestinal tract. These include tissues of the mouth, esophagus, small intestine, large intestine, rectum, and anus. Portions of these tissues such as cells composing the mucosa, submucosa or muscularis externa may be isolated and tested for content of heavy metals. Preferably, the method disclosed herein uses samples of normal, precancerous or cancerous colon or colorectal tissue, though samples may be obtained of other normal, precancerous, or cancerous gastrointestinal tissues. In one embodiment, the method as disclosed herein may be performed on a portion of a biopsy thought to be most likely cancerous, e.g., an abnormal or inflamed polyp. In other embodiments, of the disclosed method, LIBS may be performed on a sample containing a mixture of both normal and cancerous cells without the required for careful dissection of a biopsy to contain mostly cells suspected of being cancerous. Advantageously, in distinction to prior methods, the method of the invention does not require careful sampling and can detect heavy metals in any type of cancerous tissue sample.

In some embodiments, the collected samples are soaked in a composition containing a crosslinking fixative, such as formaldehyde (e.g., 10% neutral buffered formalin), glutaraldehyde, or another aldehyde; in a precipitating fixative such as methanol, ethanol, or acetone; with an oxidizing agent such as potassium permanganate; or a picrate. Preferably, a fixative is chosen that preserves the tissue sample from leaching of elements to be detected by LIES, autolysis, putrefaction or decay, but which does not contain a heavy metal or other element that would reduce the sensitivity of LIBS for the analytes such as heavy metals disclosed herein.

In some embodiments, samples may be directly analyzed or analyzed after freezing or refrigeration. The inventors observed that use of frozen samples can be advantageous because the density of ablated materials during LIES analysis is enhanced due to freezing of the sample as density is enhanced compared to a fresh, more fluid sample. However, fresh or preserved samples may be used.

Biopsy. A medical practitioner can select a biopsy method according to the type and location of the tissue to be biopsy and based on the needs or condition of the patient. Typically, a biopsy of colon tissue is obtained during a colonoscopy. However, other modes of biopsy such as needle or fine needle, CT-guided, ultra-sound guided, punch, surgical, or aspiration biopsy may be used.

A toxic heavy metal is any relatively dense metal or metalloid that is noted for its potential toxicity, especially in environmental contexts. The term has particular application to cadmium, mercury, lead and arsenic, all of which appear in the World Health Organization's list of ten chemicals of major public concern. Other examples include manganese, chromium, cobalt, nickel, copper, zinc, selenium, silver, antimony and thallium. The method as disclosed herein may be used to identify abnormal levels of toxic heavy metals in tissue samples, especially in colon or colorectal tissue samples.

Laser-induced breakdown spectroscopy (LIES) is a type of atomic emission which uses a highly energetic pulse as the excitation source. The laser is focused to form plasma, which atomizes and excites samples. The formation of the plasma only begins when the focused laser achieves a certain threshold for optical breakdown, which generally depends on the environment and the target material. In principle, LIES can analyze any material regardless of its state, be it solid, liquid or gas. All elements emit light of characteristic frequencies when excited to sufficiently high temperatures, so, in principle, LIBS can detect all elements, limited only by the power of the laser as well as the sensitivity and wavelength range of the spectrograph & detector. If the constituents of a material to be analyzed are known, LIES may be used to evaluate the relative abundance of each constituent element, or to monitor the presence of impurities. In practice, detection limits are a function of a) the plasma excitation temperature, b) the light collection window, and c) the line strength of the viewed transition. LIB makes use of optical emission spectrometry.

Ancillary treatments. If colon or colorectal cancer is detected or is at risk of developing, many treatments are available to help control it, including surgery, radiation therapy and drug treatments, such as chemotherapy, targeted therapy and immunotherapy.

Treatments for those at risk or those having early stage colon cancer include: Removing polyps during a colonoscopy (polypectomy). If the cancer is small, localized, completely contained within a polyp and in a very early stage, the doctor may be able to remove it completely during a colonoscopy.

Endoscopic mucosal resection. Larger polyps might be removed during colonoscopy using special tools to remove the polyp and a small amount of the inner lining of the colon in a procedure called an endoscopic mucosal resection.

Minimally invasive surgery (laparoscopic surgery). Polyps that can't be removed during a colonoscopy may be removed using laparoscopic surgery. In this procedure, the surgeon performs the operation through several small incisions in the abdominal wall, inserting instruments with attached cameras that display the colon on a video monitor. The surgeon may also take samples from lymph nodes in the area where the cancer is located.

Treatments for more advanced colon or colorectal cancer include:

Partial colectomy. During this procedure, the surgeon removes the part of the colon that contains the cancer, along with a margin of normal tissue on either side of the cancer. The surgeon is often able to reconnect the healthy portions of the colon or rectum. This procedure can commonly be done by a minimally invasive approach (laparoscopy).

Surgery to create a way for waste to leave the body. When it's not possible to reconnect the healthy portions of the colon or rectum, the patient may need an ostomy. This involves creating an opening in the wall of the abdomen from a portion of the remaining bowel for the elimination of stool into a bag that fits securely over the opening. Sometimes the ostomy is only temporary, allowing the colon or rectum time to heal after surgery. In some cases, however, the colostomy may be permanent.

Lymph node removal. Nearby lymph nodes are usually also removed during colon cancer surgery and tested for cancer.

Other therapies include radiation therapy, proton beam therapy, chemotherapy, targeted drug therapy, immunotherapy or palliative care.

Some commonly used chemotherapy drugs include 5-fluoruracil, oxaliplatin, irinotecan, cetuximabe, bevacizumab, panitumumab, capecitabine, and regorafenib.

In some embodiments of the invention a subject in which colon cancer or colorectal cancer is detected, or a risk of such is detected, may be treated with one or more of these therapies.

Subjects or patients. A subject may have one or more symptoms of colon or colorectal cancer or be at risk of colon cancer or colorectal cancer based on lifestyle, genetic predisposition, or family background. A patient may have no apparent symptoms of colon cancer and may have a family history with no close relatives diagnosed with colon cancer or some close relatives diagnosed with colon cancer. A patient may or may not be at increased risk of colon cancer as determined by DNA testing such detection of SNPs that correlate with a risk of colon cancer or by evaluation of DNA sequences associating with colon cancer risk as determined by full genomic DNA sequencing.

A patient may or may not have one or more symptoms of colon cancer or which indicate a risk of colon cancer, such as rectal bleeding, a change in stool color, a change in bowel habits, bowel pain, or an iron deficiency anemia resulting in fatigue and shortness of breath. Samples of colon tissue for any of such patients may be tested as disclosed herein.

Sensitivity. The method as disclosed herein can provide sensitive detection of heavy metal concentrations in colon tissue on the order of about 1 µg/L. For example, in the concentration range of about 0.25, 0.5, 0.75, 1.0, 1.25, 1.5, 1.75, 2, 2.25, 2.5, 2.75, 3, 3.25, 3.5, 3.75 to about 4 µg/L. Preferably, heavy metal concentration is measured based on the weight or mass of colon tissue tested, however, in some alternative embodiments, a concentration may be measured based on volume of the heavy metal and colon cancer tissue. The sensitivity is based on the ablation rate of the material in LIBS analysis and of course the heavy metal present in the standard sample per unit volume.

As shown by the following examples a number of cancerous and normal (healthy) colon tissue samples were collected from patients suffering from colon cancer, aged 40-60 years. Analysis of the healthy and cancerous samples was conducted by development of laser-induced breakdown spectroscopy (LIES) setup. Carcinogenic heavy metals such as mercury, chromium, and lead were detected in the malignant colon tissues, while no traces of these elements were observed in the healthy tissues. In addition to heavy metal detection, the nutrient concentrations were also determined in healthy and cancerous colon tissues.

The results obtained using the disclosed calibration-free LIES methods to detect heavy metals in malignant and healthy samples were counter-verified using a standard technique, namely Inductively Coupled Plasma Atomic Emission Spectroscopy or ICP-OES. The heavy metal concentrations detected in different samples were estimated using a calibration-free LIES method, the results of which showed strong agreement with the results obtained by the standard ICP-OES technique. These results demonstrated that LIES can be applied as a rapid diagnostic technique to differentiate between malignant and normal colon tissues.

Calibration-Free Laser-Induced Breakdown Spectroscopy (CF-LIES) provides for multi-elemental quantitative analysis of LIES spectra and is based on the measurement of line intensities and plasma parameters (plasma electron density and temperature) and on the assumption of a Boltzmann population of excited levels, which do not require the use of calibration curves or matrix-matched standards. CF-LIBS provides rapid screening of uncharacterized samples. Starting from the relative intensities of spectral lines, one constructs a number of Boltzmann plots corresponding to all constituents in the plasma. The concentration of the constituents can then be calculated from the intercepts of the lines on the y axis. One then forces the concentrations of the observed constituents to add up to 100% of the material in the plasma. The degree of accuracy of CF-LIBS results depends on several conditions including that plasma is in local thermodynamic equilibrium, is spatially homogenous and that all of the elements of the sample have lines in the spectral regions recorded by the spectrometer.

Example

LIBS setup. The description of the LIES system applied in this study is described in detail by, and incorporated by reference to the inventors' previous publications; Almessiere et al., Talanta 185(2018) 61-70; M. A. Gondal, et al., *Detection of trace metals in asphaltenes using an advanced laser-induced breakdown spectroscopy (LIBS) technique*, Energy Fuels 24(2) (2010)1099-1105; Gondal et al., J Hazard Mater 175 (2010) 726-732; Gondal et al., J. Environ. Sci. Health C 46(1) (2011)1-8; and Gondal, M. A., et al., *Detection of heavy metals in Arabian crude oil residue using laser induced breakdown spectroscopy*, Talanta, 69(5) (2006) 1072-1078, each incorporated herein by reference in their entirety.

A schematic diagram of an embodiment of this setup is presented in FIG. 1.

A Q-switched Nd:YAG laser (model QUV-266-5) was used as an ultraviolet laser excitation source. It was operated at the fourth harmonic of the Nd:YAG laser at a 266 nm wavelength, with a pulse width of 8 ns, repetition rate of 20 Hz, and maximum output energy of 50 mJ. The highly collimated laser beam with a spot diameter of approximately 0.1 mm was focused on each tissue sample placed on a two-dimensional motorized stage to allow for movement along the X-Y direction, to avoid the formation of deep craters on the target sample during the LIES analysis. That intense laser pulse generated a dense plasma plume on the tissue sample surface.

The laser-induced plasma emission signals were collected by a collimating miniature lens, which was interfaced with an optical fiber and placed at an angle of 45° with respect to the normal of the target sample. The optical fiber was connected to an optical spectrograph to disperse the plasma emission. A high-resolution 500 mm spectrograph (Andor SR 500i-A) with a grating groove density of 1199 lines/mm was used to provide effectively resolved spectral lines. The spectrograph covers a broad spectral wavelength range of 200, 300, 400, 500, 600, 700, 800 to 900 nm (ultraviolet, visible, and near-IR regions).

An intensified charge-coupled device camera (ICCD, model iStar 320T, 690×255 pixels) enabled the collection of the spectrum from the spectrograph, and directly converted that spectral (analogue) signal into a digital one. The ICCD camera is a fully integrated device comprising a high-performance digital delay generator, high-speed operated gate (or shutter), and highly sensitive camera unit. This delay generator, which is a time controller for the camera gating, was synchronized with the laser pulse. This systematic mechanism needed to be accomplished for a certain time delay, and yielded improvement in the signal-to-noise ratio (SNR) by reducing the strong background continuum plasma emissions.

Bremsstrahlung radiation, which mainly contributes to the background continuum emissions, occurs as a result of the deceleration of high-speed free electrons as they pass near a positively charged ion because of the strong electric (attractive) forces between them.

A dedicated software package (Andor SOLIS for Time Resolved: ICCD-3909) for the ICCD camera system was provided by the manufacturer. The digital signal was analyzed by the software, following which the spectrum was ready to be recorded on a PC monitor.

Sample collection and preparation for LIBS analysis. Eight surgically-excised tissue specimens, six cancerous and two normal, were obtained from patients diagnosed with colon cancer who were aged between 40 and 60 years.

Immediately following surgery, the resected tissues, which had sizes of 1.5×1.5×0.5 cm, were soaked in formalin (10% of formaldehyde in water) in a sterile specimen collection container.

The samples were transported to the laboratory and maintained in biohazard specimen plastic bags, and reusable cold ice/gel packs were laid on top of them. Thereafter, the bags were stored in a refrigerator at 4° C. for 24 to 48 h.

Prior to carrying out the experiment, the formalin was poured off and the tissue specimens were rinsed with de-ionized (DI) or distilled water a couple of times to remove any excess formalin.

The tissues were left to reach ambient room temperature and then directly placed on a glass slide for elemental analysis using LIBS.

Sample preparation for ICP-OES analysis. Approximately 50 mg of each wet tissue sample was digested in a 5 mL nitric acid solution (67-69% Fisher Scientific, USA) and left overnight in a 100 mL Pyrex beaker.

The solution was heated on a portable electric hot plate at 50 to 60° C. for 30 min to 1 h, which was sufficient to achieve complete digestion of the tissue sample and, at this level, heavy metals were released from the complex tissue matrix into the acid.

The resulting residue was then ashed at 500° C.

Thereafter, the mixture was diluted with 40 mL of DI water and further heated to 40 to 50° C. for 1 h and 30 min, finally obtaining a clear digestion solution.

Following this, the resulting solution was cooled down to room temperature and filtered with Whatman filter paper (grade no. 4) to remove any undissolved solute.

Finally, deionized (DI) water was added to the solution in a volumetric flask to obtain 100 mL of solution.

The final solution was hand-shaken and collected in translucent and chemical-resistant plastic polyethylene bottles and then stored in a refrigerator at 4° C. until the ICP-OES analysis.

The solution was analyzed for poisonous metals using an inductively coupled plasma spectrometer, calibrated using reference standards of three accuracy levels.

The same digestion procedure was used for extraction of the control (healthy) colon samples.

Determination of quantitative and qualitative elemental analysis by LIBS. Determination and selection of LIBS parameters and signal is crucial prior to carrying out elemental analysis of normal and malignant colon samples.

The inventors found that this can be attained by means of different parameters, such as those of incident laser energy and time delay. These two parameters were found to be sufficient for attaining a suitable LIBS signal intensity.

The determination of selection of a suitable "laser energy" is imperative to obtain reliable LIBS analysis, because the ablation and excitation processes in plasma depend significantly on the amount of laser energy absorbed by the target particles from the pulsed laser irradiation. Of course, this will dramatically affect the intensity of the emission lines, and consequently be reflected in the element concentrations in any target.

The LIBS technique relies mainly on the identification of trace elements, as well as the prediction of the amounts of these elements in the test sample.

An optimum time delay for our target in this experiment was investigated for chromium; specifically, the atomic line (Cr I) at 425.43 nm. This fingerprint wavelength was located in the wavelength range of 400 to 450 nm.

The signal intensity was recorded at a laser energy of 35 mJ, and an accumulation of 15 laser pulses for different time delays, from 50 to 350 ns, were investigated.

Figure 2:
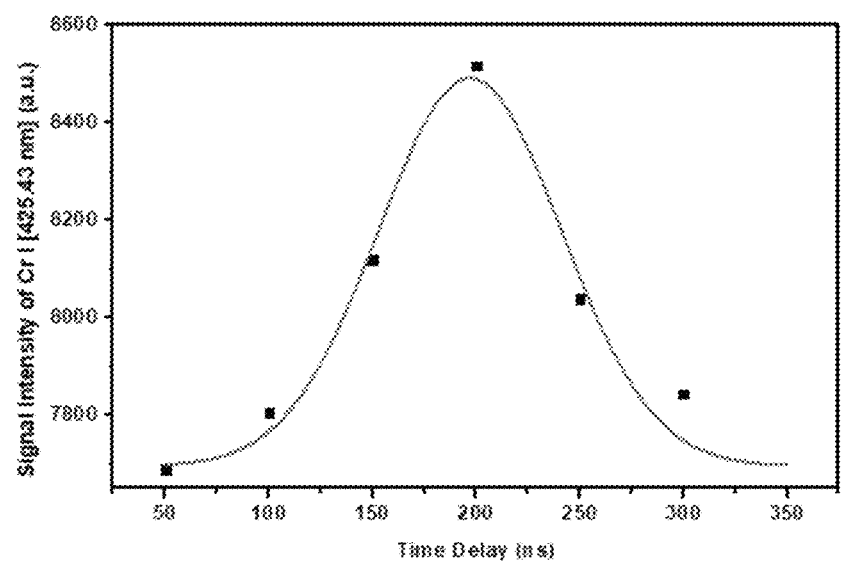
FIG. 2. Dependence of LIBS signal intensity on time delay for chromium transition line (Cr I) at 425.43 nm in malignant colon tissue sample.

The dependency of the LIBS signal intensity on the time delay is illustrated in FIG. 2. As can be observed, the signal intensity gradually increased with an increasing time delay, reaching its maximum value at 200 ns and then decreased at the same rate and producing a symmetrical line-graph. Therefore, the anticipated optimum time delay for our framework was 200 ns.

In order to study the LIES signal intensity dependence on the incident laser energy, the LIB S signal intensity was plotted against different laser energies to determine the optimum laser energy for the characteristic atomic line of chromium Cr I (425.43 nm).

For this purpose, spectra in the 400 to 450 nm wavelength range were recorded for the different laser energies (10 to 50 mJ) per pulse.

A digital laser energy meter (Ophir model 300) was used to measure the laser energy. All of the spectra were acquired by setting an accumulation of 15 laser pulses and a time delay of 200 ns.

Figure 3:
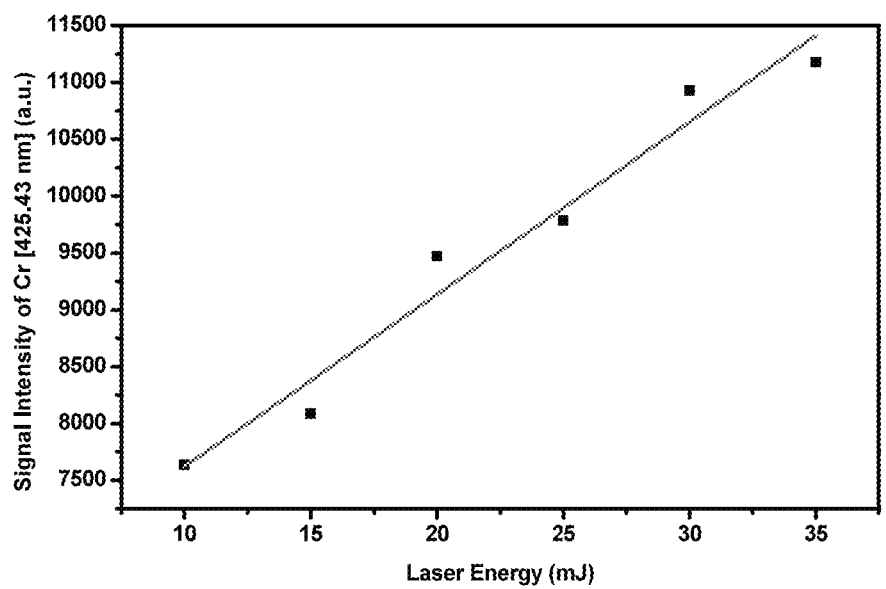
FIG. 3. Dependence of LIBS signal intensity on laser energy for chromium transition line (Cr I) at 425.43 nm in malignant colon tissue sample.

As illustrated in FIG. 3, a linear dependence of LIES signal intensity on laser energy exists; the signal intensity increases as the laser pulse energy increases from 10 to 35 mJ per pulse.

The least-square fit is calculated for the Cr I line, which is approximately 0.96 and confirms the linear dependence on the incident laser energy.

For the transition line Cr I, FIG. 3 indicates that 35 mJ is the laser energy at which the signal intensity is at its maximum. Beyond 35 mJ per pulse, the LIES signal intensity is flattened, which occurs owing to the self-absorption effect and other nonlinear processes in the laser-produced plasma.

This phenomenon occurs in plasma with a very high density. The photons emitted from atoms at a certain wavelength can be absorbed by different atoms at the ground state, resulting in a lower intensity and broadening the transition line. Resonance lines that de-excite to the ground state are more likely to be affected by self-absorption. If a strong downhill gradient in temperature occurs from the plasma center to the edges, photons emitted at the plasma center are rapidly absorbed as they pass by the colder areas. Subsequently, the center of the line is dipped, as absorption is more likely to occur at the center. At times, the line center undergoes a severe dip and the line is observed as two lines, which is a phenomenon known as "self-reversal".

Verification of local thermodynamic equilibrium for plasma generated on colon tissue sample surface. In order to achieve reliable and objective qualitative and quantitative analysis of the spectra acquired from the laser-induced plasma generated on the surface of a tissue sample, such plasma must be in local thermodynamic equilibrium (LTE).

To fulfill the state of complete thermodynamic equilibrium (CTE), the whole plasma must be homogenous with no temperature or particle density gradients.

Moreover, plasma in this equilibrium state is treated as a closed system, where no energy loss occurs and each ionization/excitation process that takes place in the plasma is equalized by its complementing mechanism.

The majority of plasma in a real laboratory is quite far from the ideal conditions of CTE. In reality, plasma is considered to be optically thin; that is, most of the photons emitted through radiative processes escape the plasma and their chances of being re-absorbed are reduced.

The total plasma volume can be divided into infinitesimal volume elements, in which the density and temperature gradients are negligible although these parameters may differ from one element to another. Then, actual plasma is set to be in LTE when it is studied over one of these elements. However, the emitted photons could still vanish from the system, so the equilibrium between the photo-ionization/absorption processes and radiative recombination/decay processes is disturbed. Therefore, the rate of the electron collisional processes in plasma must prevail over the radiative processes.

These characteristic criteria can be attained when the plasma has a high density. In such plasma, the electron collisional ionization/excitation processes are balanced by three-body recombination and collisional de-excitation processes, produced by collisions with the accelerated free electrons.

The entire thermal plasma system in CTE can be described by five equilibrium statistical distributions, which should be applied with the same temperature T While the Maxwell-Boltzmann distribution describes the velocity (energy) of all neutral and charged species constituting the plasma, the Boltzmann distribution is used for the prediction of the population of the excited levels in neutral atoms, ions, or free electrons. The Saha equation describes the ionization equilibrium and corresponding density of all of the neutral and charged species, and the Planck distribution is used to estimate the electromagnetic radiation density.

Plasma existing in LTE can be studied using the same statistical mechanics, with the exception of the Planck law, as radiation exits the plasma system. Under CTE conditions, plasma emits radiation in a wide range of wavelengths, which confirms the blackbody emission to the greatest degree. However, the plasma emission, which is investigated in a laboratory, deviates from itself by resembling the blackbody radiation. The emission is much lower as the plasma is optically thin.

Moreover, the spectral structure of the actual plasma emission is highly complex, as it is a term of superposition of discrete and narrow spectral lines over a continuum emission. Different types of transitions that produce radiation occur in the plasma. These include bound-bound transitions, where electrons move between the bound levels of an atom or ion releasing the photons that form the discrete spectral lines.

Furthermore, Bremsstrahlung and recombination radiation, which constitute continuum emission, result from free-free and free-bound transitions, respectively.

Two parameters in plasma are essential to calculate during the LIES experiment: the electron-number density and temperature. This necessity arises from the requirement for fulfilling the LTE plasma condition, whereby the electron collisional processes must dominate the radiative processes in plasma. Thus, the electron-number density must be high.

To validate this condition, the threshold electron-number density ($N_e$) for the plasma should be estimated using the McWhirter criterion. Thereafter, the experimental value of the electron-number density is measured using the Stark broadening method, and it should be equal to or greater than the threshold value. By estimating these plasma parameters (Ne and T), the LTE condition is verified.

The McWhirter criterion is expressed by the inequality below:

$$N_e \geq 1.6 \times 10^{12} T^{1/2} (\Delta E)^3,$$

where $N_e$ is the electron-number density, T is the plasma temperature, and $\Delta E$ is the energy difference between the lower and higher energy levels of the radiating particles where the transition producing the spectral lines occurs. These parameters are measured in units of cubic centimeters ($cm^{-3}$), Kelvin (K), and electron-volts (eV), respectively.

The plasma temperature T must be estimated for the McWhirter criterion. It can be obtained using the Boltzmann distribution equation:

$$\ln\left[\frac{I_{ik,Z}\lambda_{ki,Z}}{A_{ki,Z}g_{k,Z}}\right] = -\frac{E_{k,Z}}{K_B T} + \ln\left(\frac{hcLn_Z}{4\pi P_Z}\right), \tag{1}$$

where $I_{ik,Z}$ is the signal intensity of the spectral line in arbitrary units. It represents the transition between the higher energy level k and lower energy level i of the species during the ionization stage Z; that is, Z=0 and Z=1 for neutral atoms and ions, respectively. $A_{ki,Z}$ is the transition probability, while $\lambda_{ki,Z}$ is the spectral line wavelength; $g_{k,Z}$ and $E_{k,Z}$ are the degeneracy and energy, respectively, of the upper energy level k, and T is the plasma temperature. The constants $K_B$, h, and c are the Boltzmann constant ($8.6173303 \times 10^5$ eV.K$^{-1}$), Planck constant, and speed of light, respectively. Furthermore, L is the characteristic length of the plasma boundary, $n_Z$ is the relative number density, and $P_Z$ is the partition function of the species during ionization stage Z.

According to Eq. (1), a linear relationship exists between the natural logarithm function on the left-hand side of this equation and the energy $E_{k,Z}$ on the right-hand side. Thereafter, by plotting the quantity ln $$\left[\frac{I_{ik,Z}\lambda_{ki,Z}}{A_{ki,Z}g_{k,Z}}\right]$$

against $E_{k,Z}$ for multiple transitions of a specific element, a straight line with intercept ln $$\left(\frac{hcLn_Z}{4\pi P_Z}\right)$$

should be obtained it me analyzed plasma is in the LTE condition. The line slope $$\left(-\frac{1}{K_B T}\right)$$

can be employed to predict the temperature T of the plasma under investigation.

To conduct estimation of the temperature of the plasma created on the surface of a colon tissue, for malignant sample no. (1) in the LIES experiment, five and seven isolated transitions of the toxic heavy elements mercury (Hg) and chromium (Cr), respectively, were used for plotting the Boltzmann distribution equation.

Figure 4A:
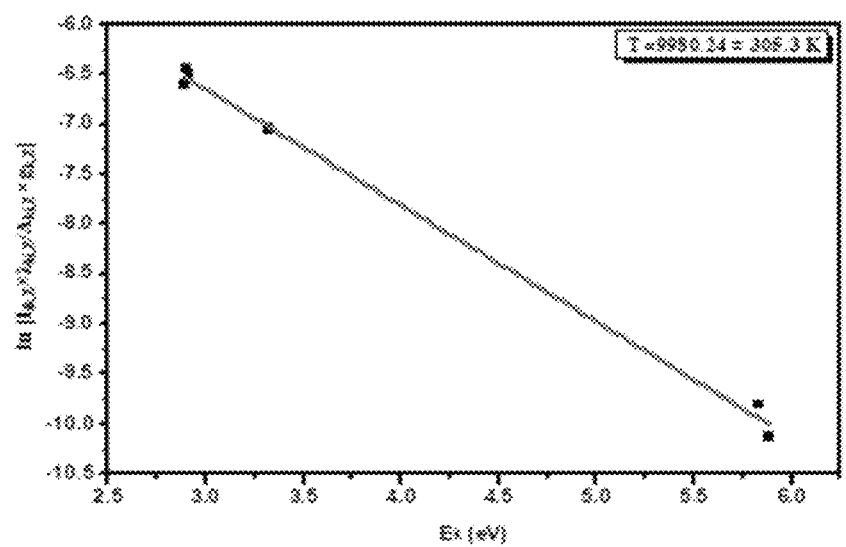
FIG. 4A: Typical Boltzmann plot for determination of plasma temperature T, where five transition lines of chromium (Cr) were used to plot the Boltzmann distribution equation.

In particular, the spectral lines with wavelengths of 425.4, 427.5, 428.9, 520.5, 520.8, 284.3, and 285.6 nm were used to plot FIG. 4A for chromium.

Table 1 lists all of the atomic spectroscopic data of the chromium transition lines; NIST Atomic Spectra Database. 2016, <hypertext transfer protocol://www.nist.gov/physlab/data/asd.cfm>, and D. R. Lide, *CRC Handbook of Chemistry and Physics*. Boca Raton, Fla., itd: CRC Press, 2003-2004 each incorporated herein by reference in their entirety.

relative higher velocities. Stark broadening also causes shifts in the energy levels of the radiating particles, which in turn shifts the spectral lines in terms of wavelengths.

The broadened line width induced by the Stark broadening increases when the lifetime of the energy levels decreases further, and this is introduced as the collision rate increases. Therefore, this type of broadening becomes notable when the plasma has a high electron density. During the first stage of plasma formation, the dominant broadening is Stark broadening, because the electron density Ne is very high (approximately $10^{-15}$ to $10^{-18}$ cm$^{-3}$) and the effects of the Doppler broadening may be negligible. However, a reduction in the number of electrons is observed once the plasma expands and cools down; hence, the Doppler width contribution is prominent and exceeds that of Stark.

The Stark broadening method enables determination of the experimentally measured electron-number density Ne of

TABLE 1

Basic atomic spectroscopic parameters of persistent transition lines of chromium (Cr) taken from NIST database for temperature estimation of laser-ablated plasma plume

| Wavelength (nm) | Element | Signal intensity | Configurations | Statistical weight $g_i$ | $g_k$ | Transition probability $A_{ik} \times 10^8$ (S$^{-1}$) | Energy of upper level $E_i$ (eV) | $E_k$ (eV) |
|---|---|---|---|---|---|---|---|---|
| 425.4 | Cr I | 1000 | 3d$^5$($^6$S) 4s a$^7$S$_3$→<br>3d$^5$ ($^6$S) 4p z$^7$P°$_4$ | 7 | 9 | 0.315 | 0 | 2.9 |
| 427.5 | Cr I | 800 | 3d$^5$($^6$S) 4s a$^7$S$_3$→<br>3d$^5$ ($^6$S) 4p z$^7$P°$_3$ | 7 | 7 | 0.307 | 0 | 2.9 |
| 428.9 | Cr I | 500 | 3d$^5$($^6$S) 4s a$^7$S$_3$→<br>3d$^5$ ($^6$S) 4p z$^7$P°$_2$ | 7 | 5 | 0.316 | 0 | 2.9 |
| 520.5 | Cr I | 250 | 3d$^5$($^6$S) 4s a5S$_2$→<br>3d$^5$ ($^6$S) 4p z$^5$P°$_1$ | 5 | 3 | 0.509 | 0.9 | 3.3 |
| 520.8 | Cr I | 600 | 3d$^5$($^6$S) 4s a$^5$S$_2$→<br>3d$^5$ ($^6$S) 4p z$^5$P°$_3$ | 5 | 7 | 0.506 | 0.9 | 3.3 |
| 284.3 | Cr II | 90 | 3d$^4$($^5$D) 4s a$^6$S$_{7/2}$→<br>3d$^4$ ($^5$D) 4p z$^6$P°$_{9/2}$ | 8 | 10 | 0.6 | 1.5 | 5.9 |
| 285.6 | Cr II | 50 | 3d$^4$($^5$D) 4s a$^6$S$_{3/2}$→<br>3d$^4$ ($^5$D) 4p z$^6$P°$_{5/2}$ | 4 | 6 | 0.4 | 1.5 | 5.8 |

The total linearity depicted in FIG. 4A confirms the assumption that the ablated plasma of the colon tissue satisfies the LTE condition, and a temperature of 9980.2±305.3 K for Cr can easily be deduced using the line slope. Thereafter, the threshold electron density was calculated using the McWhirter criterion for the neutral atomic lines of chromium (Cr I) at 425.4 nm, which is 0.4×10$^{16}$ cm$^{-3}$, respectively. The spectral line is naturally broadened owing to the Heisenberg uncertainty principle. This line can be broadened further depending on two factors: the temperature and electron-number density. The thermal motion of the emitters, atoms, and ions in the plasma causes the line to be broadened and exhibit a Gaussian shape. This broadening is known as "Doppler broadening", and the resulting line width is directly proportional to the square root of the temperature. The dominance of Doppler broadening is significant in plasma with a low electron density. Another broadening mechanism, namely "Stark broadening", results from the disturbance of the excited energy levels of the emitters when these emitters interact with the electric microfields of the surrounding charged particles; that is, ions and free electrons. Both the natural and Stark broadenings produce lines with a Lorentzian profile; Fridman, L. A. Kennedy, Plasma physics and engineering, CRC press, 2004. The contribution of free electrons to the broadening is substantially more noticeable than for ions because of their the plasma. This method is used because the Stark effect is the main source of broadening of the spectral line in plasma with a high number of free electrons. The collisional processes are then incomparable (very high) to the radiative processes, and the LTE state is achieved. Therefore, the plasma is optically thin and any chance of the occurrence of self-absorption is reduced.

For a Stark-broadened spectral line of non-hydrogenic neutral atoms and ions, the Full width at half maximum (FWHM), $\Delta\lambda_{1/2}$, measured in A°, is provided by Eqs. (2) and (3), respectively:

$$\Delta\lambda_{1/2} = 2w\left[\frac{N_e}{10^{16}}\right] + 3.5A\left[\frac{N_e}{10^{16}}\right]^{5/4}\left[1 - \frac{3}{4}N_D^{-1/3}\right]w \quad A° \quad (2)$$

$$\Delta\lambda_{1/2} = 2w\left[\frac{N_e}{10^{16}}\right] + 3.5A\left[\frac{N_e}{10^{16}}\right]^{5/4}\left[1 - \frac{6}{5}N_D^{-1/3}\right]w \quad A°, \quad (3)$$

where w is the Stark width coefficient of the spectral line, A is the ion broadening parameter, $N_D$ is the number of particles in the Debye sphere, and $N_e$ is the electron-number density measured in cm$^{-3}$. The first term on the right-hand side of both Eqs. (2) and (3) represents the symmetric Lorentzian profile of the spectral line resulting from multiple electron impacts, while the second term reveals the corrections of the asymmetric spectral profile, caused by the electric micro-fields of ions. As mentioned previously, the perturbations caused by free electrons exceed those induced by slowly moving ions; thus, Eqs. (2) and (3) can be rewritten as:

$$\Delta\lambda_{1/2} \cong 2w\left[\frac{N_e}{10^{16}}\right] A°. \quad (4)$$

Figure 4B:
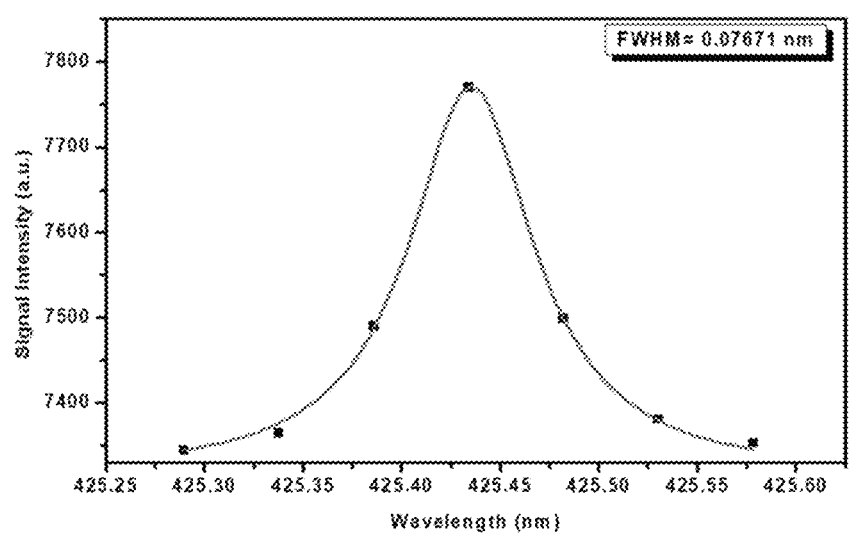
FIG. 4B: Typical Stark broadening profile for transition line of chromium (Cr I) at 425.4 nm plotted for determination of electron density (Ne).
Figure 5A:
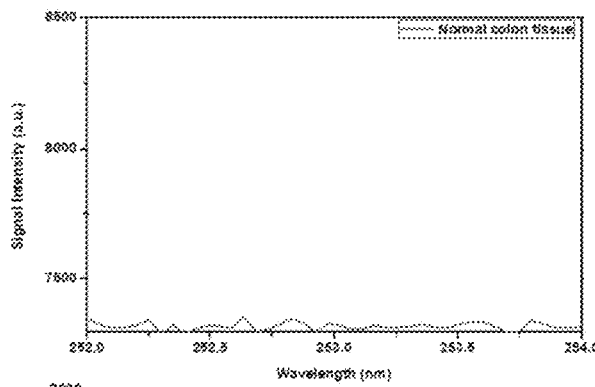
FIGS. 5A-5D. Atomic lines of Hg I 253.7 nm in malignant (FIGS. 5B-5D) and normal (FIG. 5A) tissues.
Figure 5B:
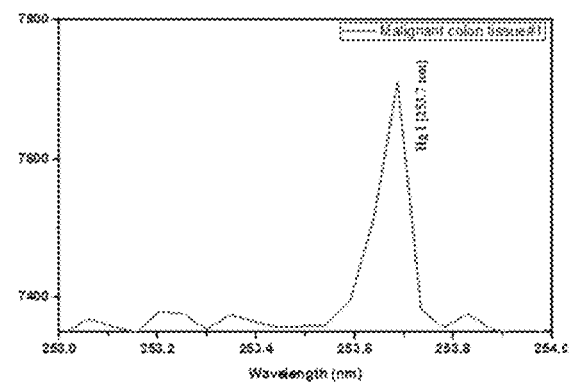
Figure 5C:
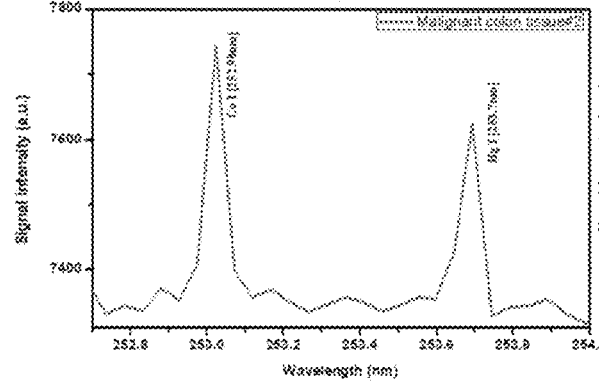
Figure 5D:
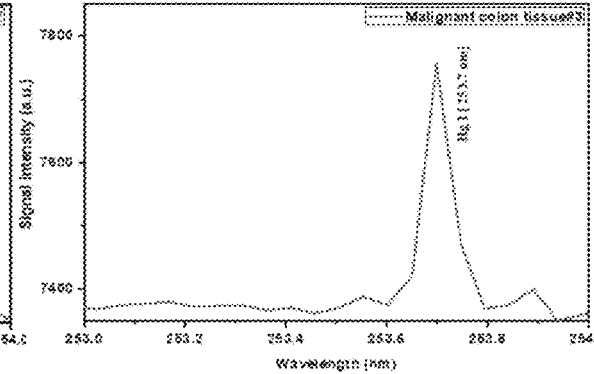
Figure 6A:
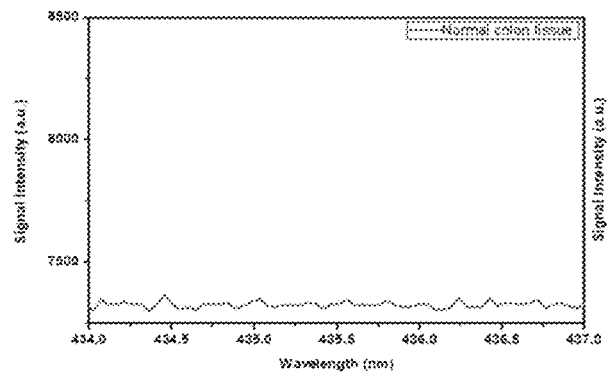
FIGS. 6A-6D. Atomic line of Hg I 435.8 nm in malignant (FIGS. 6B-6D) and normal (FIG. 6A) tissues.
Figure 6B:
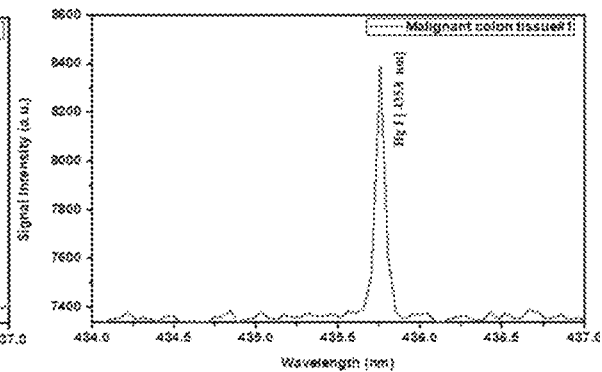
Figure 6C:
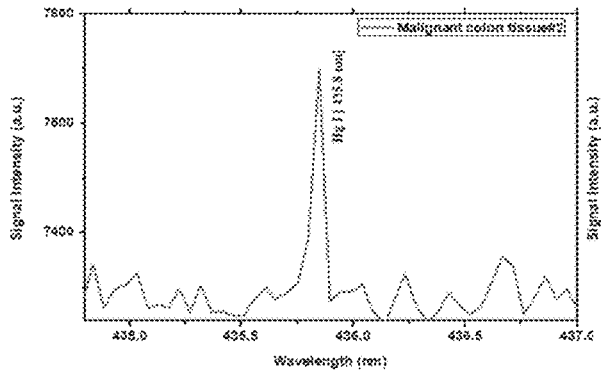
Figure 6D:
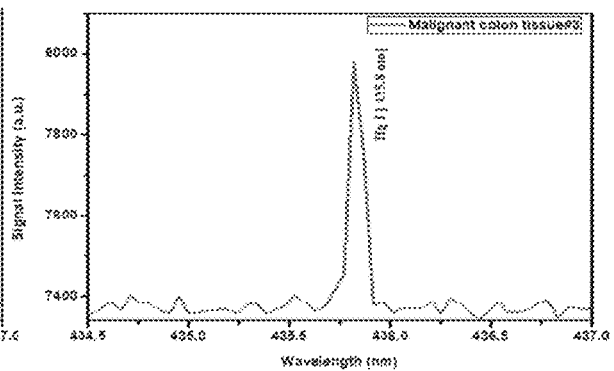
Figure 10A:
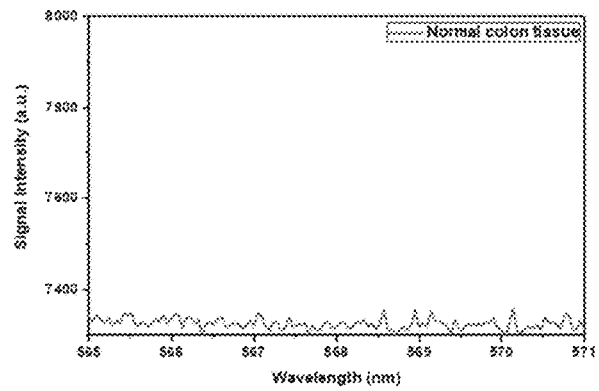
FIGS. 10A-10D. Atomic lines of Ce I 566.9, 569.9, and 571.9 nm in malignant (FIGS. 10B-10D) and normal (FIG. 10A) tissues.
Figure 10B:
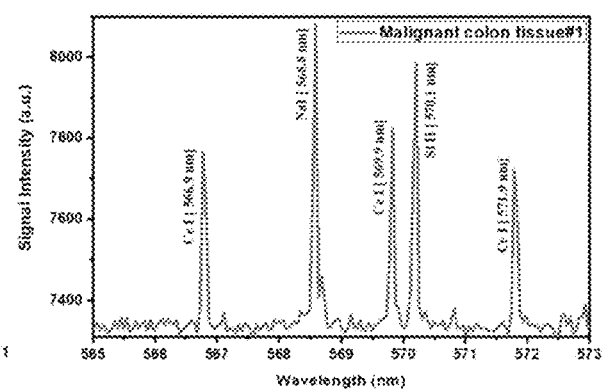
Figure 10C:
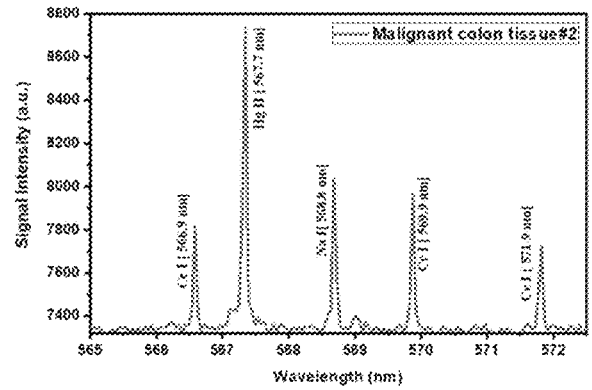
Figure 10D:
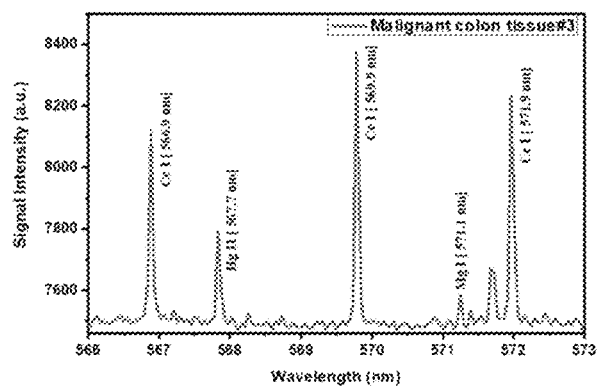

Equation 4 above relates the FWHM of a spectral line to the electron-number density $N_e$. Hence, a Lorentzian-fitted isolated transition line is used to measure the plasma electron-number density. The neutral chromium (Cr I) spectral lines at 425.4 nm was selected for this purpose. The FWHM of the chromium 425.4 nm line in FIG. 4B was measured, and it was equal to 0.07671 nm. It was difficult to find a published reference concerning the Stark broadening coefficient or Stark FWHM for Cr I and Cr II transition lines.

An experimental Stark width (in angstrom) was reported for 24 neutral and singly ionized atomic lines of chromium in the work carried out by Diego; Marton, L. (Ed.). (1970). *Plasma Physics. Methods of Experimental Physics*, Volume 9. Elsevier Science & Technology, incorporated herein by reference in its entirety. The values actually varied within a very small range. This method was unable to calculate the plasma electron density owing to scarce data regarding the Stark broadening coefficient, but it was projected to be $10^{17}$ from previous work with similar experimental conditions. As this was the only reliable work on chromium lines, the Stark broadening coefficient for the 425.4 nm line was estimated to 0.004 A° from a line with almost similar transition.

By substituting the FWHM of the chromium line in our experiment and Stark broadening coefficient value into Eq. (4), the electron number density was calculated as $9.6 \times 10^{17}$ $cm^{-3}$ for 425.4 nm. By comparing the estimated electron density for Cr I line with the threshold value, it was concluded that the former were greater than the latter value provided by the McWhirter criterion. Based on the inventors' analysis, the ablated plasma of the colon tissue sample in our LIBS experiment can be guaranteed to obey the LTE requirements.

LIBS qualitative analysis of normal and malignant tissues. The LIES spectra were collected from two control (healthy) and six malignant tissues of volunteer female patients, with ages ranging from 40 to 60 years. The spectra were obtained for every 50 nm. The time delay, incident laser energy, and number of accumulations were adjusted to improve the signal quality and minimizing the background noise that could affect the analysis. The samples are analyzed by LIES to determine a correlation between the accumulations of certain atomic transition lines of particular toxic elements responsible for the development of malignancy in colon tissues.

Table 2 depicts the intensities of the persistent lines of the detected elements.

TABLE 2

Intensities of persistent lines of detected elements

| Element | Fingerprint wavelengths (nm) | LIBS intensity (a.u.) | | | | |
|---|---|---|---|---|---|---|
| | | Malignant colon tissue 1 | Malignant colon tissue 2 | Malignant colon tissue 3 | Malignant colon tissue 4 | Normal colon tissue |
| Ca II | 393.4 | 7808.9 | 7461.0 | 7704.7 | 7938.9 | 8379.56 |
| | 396.8 | 7712.6 | 7502.7 | 8173.6 | 8193.4 | 7854.38 |
| Ca I | 422.7 | 8611.6 | 7888.6 | 9016.3 | 8153.9 | 8483.57 |
| K I | 766.5 | 7544.8 | 7566.7 | 7986.5 | 8467.9 | 7738.61 |
| | 769.9 | 7612.2 | 7708.5 | 7726.7 | 8238.1 | 7663.75 |
| Na I | 588.9 | 7769.4 | 7952.7 | 11416.9 | 7908.2 | 61719.3 |
| | 589.6 | 7513.3 | 7721.9 | 6051.9 | 7623.4 | 46113.4 |
| Hg I | 253.7 | 7713.8 | 7627.4 | 7757.3 | 7703.4 | ND (not detected) |
| Hg I | 435.8 | 8399.7 | 7551.8 | 7905.1 | 7831.3 | ND |
| Pb II | 220.4 | 7778.5 | 7705.8 | 8065.6 | 8192.6 | ND |
| Pb I | 405.8 | 8180.8 | 7692.9 | 7627.3 | 8046.2 | ND |
| Cr I | 357.9 | 7662.1 | 7746.5 | 7932.6 | 8833.5 | ND |
| | 359.3 | 7543.3 | 7537.7 | 7750.8 | 8656.9 | ND |
| | 360.5 | 7412.2 | 7403.9 | 7446.7 | 7611.3 | ND |
| Cr I | 425.4 | 7873.9 | 7974.6 | 7796.7 | 7796.7 | ND |
| | 427.5 | 7630.1 | 7753.5 | 7709.5 | 7527.1 | ND |
| | 428.9 | 7489.4 | 7560.0 | 7543.2 | 7433.2 | ND |
| Ce I | 515.9 | 7859.4 | 7541.9 | 8021.8 | 7817.7 | ND |
| | 516.1 | 8074.6 | 7631.8 | 8125.5 | 7657.2 | ND |
| Ce I | 566.9 | 7716.2 | 7822.3 | 8123.5 | 8317.5 | ND |
| | 569.9 | 7826.9 | 7965.9 | 8373.7 | 8569.2 | ND |
| | 571.9 | 7681.5 | 7726.1 | 8240.1 | 7912.6 | ND |

In one embodiment, of the invention, prior to colon or colorectal tissue collection, the patient is administered a loading dose of an element that is preferentially adsorbed by colon cancer or colorectal cancer cells for a time and under conditions sufficient for the cancer tissue to adsorb the element. Such a dose may also be present due to prior treatment or diagnosis, for example, cerium or other elements may be present in non-healthy and cancerous tissues in part due to presence in medications or contrast agents. Subsequently, a tissue sample is acquired and the LIBS-based method disclosed herein is performed. A loading dose is administered in a manner suitable to permit colon or colorectal cancer cells to adsorb the element, such as Ce (or other lanthanides), Si or Nd (or other rare earth element), for example, orally or rectally, or parenterally. Examples of such compounds include salts of these metals, such as halides, oxides, sulfides, nitrides, hydroxides, phosphides, nitrates and sulfates. LIES can excite and detect multiple elements simultaneously.

The LIES spectra of the tissues exhibited atomic and ionic spectral lines of numerous elements, including calcium, sodium, potassium, lead, mercury, chromium, and cerium. As shown herein, the inventors primarily focused on toxic elements such as lead, mercury, and chromium. The accumulation of these toxic elements may cause radical formations and DNA damage which may be implicated in the pathophysiology of cancer. The relative peak heights or ratio of different peaks to each other is indicator for accumulation of more toxic heavy metals which may be attributed to aging of cancerous tissue and more exposure of person to these heavy metals due to intake of certain food or living in different environment.

A slight increase in the intensity of the transition lines Cr 357.9, Ce 566.9, and Ce 569.9 nm was observed from malignant tissue samples 1 to 4.

However, the intensities of the lead and mercury exhibited no remarkable variations for the malignant tissues.

The atomic lines of Hg I 253.7 nm and 435.8 nm in the malignant and normal tissues are depicted in FIGS. 5 and 6, respectively.

The atomic lines of Pb I 220.4 nm and 405.8 nm in the malignant and controlled tissues are depicted in FIGS. 7 and 8, respectively.

The atomic lines of Cr I in the malignant and normal tissues are depicted in FIG. 9.

The atomic lines of Ce I 569.9, 569.9, and 571.9 nm in the malignant and normal tissues are depicted in FIG. 10.

LIBS quantitative analysis of control and malignant tissues. The results achieved by the analytic technique of LIBS were verified with another conventional analytical method for elemental analysis, namely inductively coupled plasma-atomic emission spectroscopy (ICP-OES), which was carried out using the ICP plasma atomic emission spectrometer from Shimadzu.

For the ICP-OES, tissue samples were prepared using the conventional wet acid method (CDM). Directly prior to digestion of the tissue specimens, they were partially thawed, and a thick layer of the tissue surface was cut off from each sample to remove any contaminants stuck thereto or any debris arising in the tissue during the LIB S investigation.

Moreover, any membranes, fatty tissues, and blood vessels found on the tissue were removed before starting the digestion procedure. Furthermore, all used glassware and plastics for the digestion procedure should be soaked for 24 h in a 10% nitric acid solution, washed numerous times with DI water, dried, properly covered, and stored in a clean and contamination-free area; R. Rahil-Khazen, B. J. Bolann, A. Myking, R. J Ulvik, *Multi-element analysis of trace element levels in human autopsy tissues by using inductively coupled atomic emission spectrometry technique (ICP-AES)*, J. Trace Elem. Med. Biol. 16(1) (2002) 15-25) (incorporated herein by reference).

All elements that were detected in the malignant and controlled samples by LIB S were presented through the ICP, except for mercury due to the unavailability of the hydride generation system combined with ICP-OES. The ICP values are recorded in Table 3, which indicates that the ICP results correspond to the LIBS in terms of the presence of all fingerprint elements.

TABLE 3

ICP-OES calibrations of trace elements in malignant and normal tissues

| Element | Fingerprint Wavelengths (nm) | ICP concentration (μg/L) | | | | |
|---|---|---|---|---|---|---|
| | | Malignant colon tissue 1 | Malignant colon tissue 2 | Malignant colon tissue 3 | Malignant colon tissue 4 | Normal colon tissue |
| Pb I | 405.8 | 2.7 | 2.7 | 2.7 | 2.7 | BDL (below detection limit) |
| Cr I | 427.5 | 14.6 | 14.6 | 14.6 | 14.6 | BDL |
| Ce I | 569.9 | 3.2 | 3.2 | 3.2 | 3.2 | BDL |

Calibration free LIBS. The calibration curve method exhibits certain limitations, because in many cases, to obtaining a sample matrix that is similar to an unknown matrix is impossible. To overcome this ambiguity, calibration-free (CF)-LIES can be applied under two conditions: the plasma is optically thin and at LTE during collection of the plasma spectrum. The electron-number density and plasma temperature measured verified that the plasma was optically thin and in LTE. Hence, CF-LIBS was applied to quantify the element contents by means of the estimation of the plasma temperature, electron density, and relative number density of neutral and singly ionic species, utilizing the experimental spectral line intensities of the plasma emissions. The advantage of this method was that the need for matching the sample matrix or calibration-based LIES is eliminated.

The integral intensity of the measured spectral line can be expressed as:

$$I_\lambda^{ki} = FC_S A_{ki} \frac{g_k}{U_S(T)} \exp\left(\frac{-E_k}{K_B T}\right), \quad (5)$$

where k and i are the indices of the upper and lower transition levels, $\lambda$, is the wavelength corresponding to the transition between the upper energy level $E_k$ and lower energy level $E_i$, F is an experimental parameter that takes into account the optical efficiency of the collection system, as well as the total plasma density, and $C_s$ is the concentration of the emitting species s. Furthermore, $A_{ki}$ is the transition probability for spontaneous emission from state k to i, $g_k$ is the degeneracy of the k level, $K_B$ is the Boltzmann constant, T is the plasma temperature, and $U_s(T)$ is the partition function of the emitting species s at the plasma temperature T, which can be calculated using Eq. 6:

$$U(T) = \sum g_k \exp\left(\frac{-E_k}{K_B T}\right), \quad (6)$$

The spectral parameters can be obtained from the National Institute of Standards and Technology (NIST)

database, and the values of F, $C_s$, and T can be determined from the experimental data listed in Tables 1 and 2. See NIST Atomic Spectra Database. 2016, <hypertext transfer protocol://www.nist.gov/physlab/data/asd. Table 4. CF-LIBS and ICP-OES calibrations of trace elements in malignant tissue cfm>, incorporated herein by reference in its entirety. Thereafter, the F factor can be determined by normalization to unite the sum of the species concentrations.

$$\sum_S C_S = \frac{1}{F} U_s(T) \exp(q_S) = 1, \quad (7)$$

where $$q_S = \ln\left(\frac{C_S F}{U(T)}\right).$$

Finally, the concentration of the species s in the sample can be obtained by $$C_S = \frac{1}{F} U_s(T) \exp(q_s), \quad (8)$$

The results of the CF-LIBS for sample 1 compared to ICP-OES are listed in Table 4. The results of the CF-LIBS are in strong agreement with the standard method of ICP-OES. As the detection of Hg was not possible using ICP-OES due to its high volatility; however, this was carried out using CF-LIES calculations, and the concentration was found to be 11.6 µg/L for Hg I 253.7 nm.

The existence of cancerous elements such as lead, mercury, and chromium are listed in Table 4 from the CF-LIES and ICP-OES analysis of trace elements for malignant tissue sample 1.

TABLE 4

CF-LIBS and ICP concentration (µg/L) for sample 1

| Element | Fingerprint wavelengths (nm) | CF-LIBS | ICP |
|---|---|---|---|
| Pb I | 405.8 | 3.1 | 2.7 |
| Cr I | 427.5 | 13.4 | 14.6 |
| Ce I | 569.9 | 3.1 | 3.2 |

Comparison of data from two detection techniques and LIBS accuracy. The LIBS system disclosed herein attained superior accuracy and precision. A sufficient warm-up time was permitted for the laser to be stabilized prior to starting the measurements to avoid laser pulse fluctuations. The LIES spectra were averaged for 20 laser pulses, as the relative standard deviation decreased with an increase in the number of laser shots.

The relative accuracy (RA) is calculated as follows:

$$RA = \frac{|d| + SD \times \frac{t_{0.975}}{\sqrt{n}}}{M}, \quad (9)$$

where d is the difference between the LIBS and ICP data (standard method), SD is the standard deviation of the LIES measurement, M is the measurement from the ICP-AE standard method, n is the number of measurements, and $t_{0.972}$ is the t-value at a 2.5% error confidence. See M. G. Natrellla, *Experimental Statistics*, NBS Handbook 91, National Institute of Standards and Technology, Gaithessburg, Md., 1963, incorporated herein by reference in its entirety. The data in Table 5 show that the relative accuracy is within the range of 0.03 to 0.5 which is quite acceptable for any effective instrument.

TABLE 5

Elements detected in malignant tissues and comparison of CF-LIBS with ICP

| Elements detected in malignant tissues | Wave-length (nm) | Comparison of LIBS and ICP, and RA | | | Standard deviation LIBS |
|---|---|---|---|---|---|
| | | CF-LIBS µg/L | ICP µg/L | RA | |
| Pb I | 405.8 | 3.1 | 2.7 | 0.54 | 0.12 |
| Cr I | 427.5 | 13.4 | 14.6 | 0.64 | 0.13 |
| Ce I | 569.9 | 3.1 | 3.2 | 0.03 | 0.09 |

Heavy metals may have a significantly harmful effect on human being bodies even at low levels. They affect chromatin by interfering with various nuclear proteins, changing their activity profiles, which may lead to DNA gene deformation and carcinogenesis. As shown herein the LIBS and ICP-OES techniques can be successfully employed to detect the existence of cancerous heavy elements in numerous malignant and normal (control) colon tissue. All observations demonstrated that LIES is a reliable technique for sensitively detecting heavy elements such as Hg, Cr, and Pb in cancerous tissues. The inventors found that these heavy metals accumulate in the malignant tissues, whereas there was no detection of these elements in the control (healthy) samples. Each element was identified via the NIST database. See NIST Atomic Spectra Database (2016, incorporated by reference). Moreover, the inventors confirmed that accuracy of their LIES results using the ICP-OES method to determine the consistency between LIES and ICP. The electron temperature and electron density were estimated for the plasma produced from the malignant and control tissues by focusing on specific elements such as Hg and (Cr). The inventors found a correlation in results between CF-LIES and the standard technique of ICP-OES.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A method for distinguishing normal, non-cancerous colon or colorectal tissue from cancerous colon or colorectal tissue comprising:
    applying laser induced breakdown spectroscopy ("LIBS") to one or more test samples of colon or colorectal tissue,
    comparing a signal intensity for at least one heavy metal in the test sample of colon or colorectal tissue from a subject with a signal intensity for said heavy metal in a control sample, and
    selecting a subject having, or at risk of having, colon or colorectal cancer when the signal intensity for the heavy metal in the test sample is greater than that for the same heavy metal in the control sample; and,
    optionally treating the selected subject for colon cancer or colorectal cancer,
    wherein the heavy metal is cerium (Ce) and atomic lines (or peak value) at 566.9, 567.7, 569.9 and/or 571.9 nm are detected.

2. The method of claim 1, wherein the test sample and control samples are colon tissue.

3. The method of claim 1, wherein the test sample and control samples are colorectal tissue.

4. The method of claim 1, wherein the test sample is a polyp.

5. The method of claim 1, wherein the test sample is inflamed colon or colorectal tissue.

6. The method of claim 1, wherein the subject has a family history of colon or colorectal cancer or wherein the subject is at higher risk of colon or colorectal cancer based on DNA sequencing data.

7. The method of claim 1, further comprising:
    comparing a signal intensity of at least one of calcium (Ca), potassium (K) or sodium (Na) in the test sample of the colon or colorectal tissue with an intensity of the same elements in the control sample; and
    selecting a subject having, or at risk of having, colon or colorectal cancer when the signal intensity for the Ca, K or Na in the test sample is greater than that for the same element in the control sample.

8. The method of claim 1, wherein said LIBS use a laser intensity that ranges from about 25 to 50 mJ.

9. The method of claim 1, wherein said LIBS uses a laser intensity of about 35 mJ.

10. The method of claim 1, wherein said LIBS comprises about 5 to 25 laser pulses having time delays ranging between 50 and 350 ns.

11. The method of claim 1, wherein said LIBS comprises a laser intensity of about 35 mJ, and about 10 to 20 laser pulses having time delays of about 200 ns.

* * * * *